(12) United States Patent
Lazarus

(10) Patent No.: US 6,544,268 B1
(45) Date of Patent: *Apr. 8, 2003

(54) DELIVERY SYSTEM WITH BALLOON CATHETER

(75) Inventor: Harrison M. Lazarus, Salt Lake City, UT (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/542,035

(22) Filed: Apr. 3, 2000

Related U.S. Application Data

(60) Continuation of application No. 09/405,965, filed on Sep. 27, 1999, which is a continuation of application No. 08/748,637, filed on Nov. 13, 1996, which is a continuation of application No. 08/342,438, filed on Nov. 18, 1994, now Pat. No. 5,662,700, which is a continuation of application No. 08/175,491, filed on Dec. 29, 1993, now Pat. No. 5,397,345, which is a continuation of application No. 08/034,587, filed on Mar. 22, 1993, now abandoned, which is a continuation of application No. 07/752,058, filed on Aug. 29, 1991, now abandoned, which is a division of application No. 07/166,093, filed on Mar. 9, 1988, now Pat. No. 5,104,399.

(51) Int. Cl.⁷ .................................................. A61F 2/06

(52) U.S. Cl. ...................................... 606/108; 623/1.11

(58) Field of Search ................................ 606/192, 194, 606/108, 200; 623/1.11, 1.13, 1.14

(56) References Cited

U.S. PATENT DOCUMENTS 5,266,073 A * 11/1993 Wall .............................. 623/1

FOREIGN PATENT DOCUMENTS

SU              660680      *  8/1979   ..................... 623/1

* cited by examiner

Primary Examiner—Bruce Snow
(74) Attorney, Agent, or Firm—Fulwider Patton Lee & Utecht, LLP

(57) ABSTRACT

An intraluminal grafting system includes a hollow graft which has a proximal staple positioned proximate its proximal end and a distal staple adapted proximate its distal end. The system includes a capsule for transporting the graft through the lumen and for positioning the proximal end of the graft upstream in a lumen which may be a blood vessel or artery. A tube is connected to the capsule and extends to exterior the vessel for manipulation by the user. A catheter is positioned within the tube to extend from the cavity and through the graft to exterior the body. The catheter has an inflatable membrane or balloon proximate the distal end thereof which is in communication via a channel with inflation and deflation means located exterior the vessel. With the inflatable membrane deflated, the capsule is positioned in the lumen and manipulated to a desired location. The inflatable membrane is manipulated by the rod away from the graft. The force exerted by the inflatable membrane and the structure of the staples urges the staples in the vessel wall, retaining the graft in position. The remainder of the intraluminal grafting system is then removed from the corporeal vessel.

9 Claims, 5 Drawing Sheets

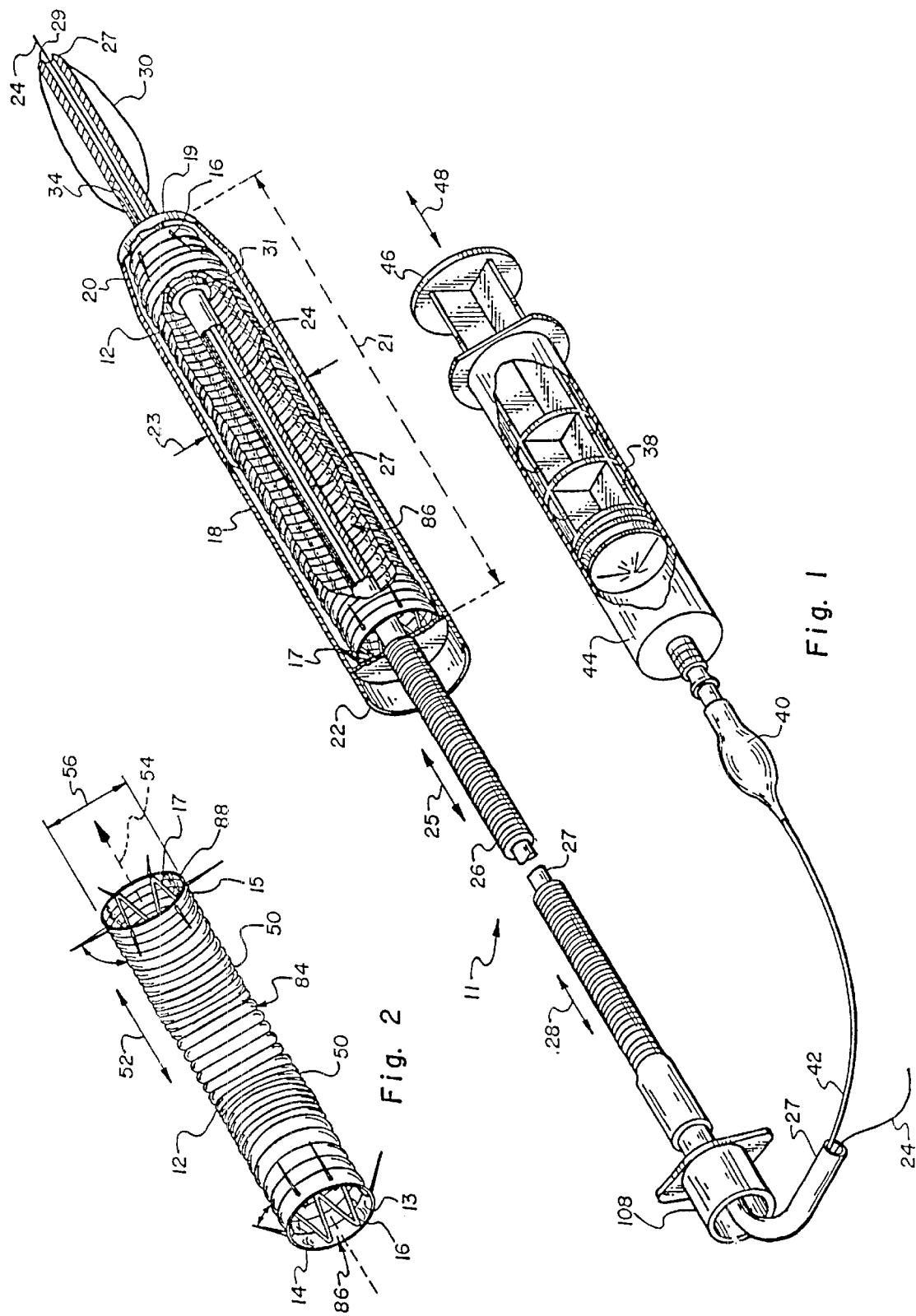

US 6,544,268 B1

DELIVERY SYSTEM WITH BALLOON CATHETER

RELATED APPLICATIONS

This application is a continuation of application Ser. No. 09/405,965, filed Sep. 27, 1999, which is a continuation of application Ser. No. 08/748,637, filed Nov. 13, 1996, which is a continuation of application Ser. No. 08/342,438, filed Nov. 18, 1994, now U.S. Pat. No. 5,662,700, which is a continuation of application Ser. No. 08/175,491, filed Dec. 29, 1993, now U.S. Pat. No. 5,397,345, which is a continuation of application Ser. No. 08/034,587, filed Mar. 22, 1993, now abandoned, which is a continuation of application Ser. No. 07/752,058, filed Aug. 29, 1991, now abandoned, which is a divisional of application Ser. No. 07/166,093, filed Mar. 9, 1988, now U.S. Pat. No. 5,104,399.

BACKGROUND OF THE INVENTION

1. Field

This invention relates to a medical prosthesis and, more particularly, to a graft prosthesis for placement within in a corporeal lumen, such as the lumen of a blood vessel or artery.

2. State of the Art

Various fluid conducting body lumens, such as veins and arteries, may deteriorate or suffer trauma so that repair is necessary. For example, various types of aneurysms or other deteriorative diseases may affect the ability of the lumen to conduct fluids and in turn may be life-threatening. In some cases, the damaged lumen is repairable only with the use of prosthesis such as an artificial vessel or graft.

For repair of vital vessels such as the aorta, surgical repair is significantly life-threatening. Surgical techniques employed involve major surgery in which an artificial section of vessel is spliced into the diseased or obstructed lumen. That is, the damaged or diseased portion of the lumen may be surgically removed or bypassed and an artificial or donor graft inserted and stitched to the ends of the vessel which were created by the removal of the diseased portion. Kaj Johansen, *Aneurysms,* Scientific American, 247:110–125, July 1982. A variation of the typical suturing technique is described by Albert W. Krause, et al., *Early Experience with Intraluminal Graft Prosthesis,* American Journal of Surgery, 145:619–622, May 1983. The device illustrated in U.S. Pat. No. 3,908,662 to Razgulov, et al. is an example of a device to be used in such a surgical procedure.

Other devices for the repair of lumens or vessels such as veins and arteries include a nitinol coil with a graft. The nitinol coil is reduced in dimension when cool. When placed in the body its temperature increases, and it returns to a preselected dimension to hold a graft within the lumen of the vessel. Such devices are discussed in detail in Charles T. Dottner, et al., *Transluminal Expandable Nitinol Coil Stent Grafting: Preliminary Report,* Radiology 147:259–260, April 1983, and Andrew Cragg, et al., *Nonsurgical Placement of Arterial Endoprostheses: A New Technique Using Nitinol Wire,* Radiology 147:261–263, April 1983. The use of devices such as the previously discussed nitinol wire may not be desirable due to the danger of penetrating and damaging the vessel's wall during the emplacement process.

U.S. Pat. No. 4,140,126 to Choudhury discloses a device for intraluminal repair of an aneurysm. This device is positioned in a vessel in a collapsed form and then hooked into the vessel with hooks that are mechanically extended by the user. This device is mechanically complex and in turn is susceptible to mechanical failure.

Other intraluminal devices are known, for uses other than the repair of a diseased lumen or vessel. U.S. Pat. No. 3,874,388 to King, et al. discloses a system for closing off a septal defect or shunt in the intravascular system in the myocardial area. U.S. Pat. No. 3,334,629 to Cohn discloses a device for restricting the flow of blood. U.S. Pat. No. 4,056,854 to Boretus, et al. teaches construction and placement of an artificial aortic heart valve. U.S. Pat. No. 3,834,394 to Hunter et al. teaches construction of an intraluminal device to occlude a blood vessel. U.S. Pat. No. 3,540,431 to Mobin-Uddin teaches construction of an umbrella-like filter for intraluminal use. MEDI-TECH, Inc. of Watertown, Mass. sells a device known as the GREENFIELD Vena Cava filter for intraluminal placement. U.S. Pat. No. 3,938,528 discloses a device that is implanted into the vas-deferens or similar lumen for the splicing of the lumen parts.

None of the devices noted above disclose a reliable and quick means or method to repair a vessel intraluminally.

SUMMARY OF THE INVENTION

An artificial intraluminal prosthesis for placement in a fluid conducting corporeal lumen has a hollow graft of preselected cross-section and length. The proximal end of the graft is placed upstream within the lumen. The graft is deformable to conform substantially to the interior surface of the lumen. Staples are attached to the proximal end and preferably to the distal end of the graft for stapling the graft to the wall of the lumen.

Each staple has wall engaging members. The wall engaging members of the proximal staple are generally angulated in a downstream direction and have tips for engaging the vessel wall. The wall engaging members of the distal staple are angulated in a direction generally perpendicular to the longitudinal or central axis of the graft, and also have tips for engaging the wall.

Generally, the staples are formed into a V-shaped lattice or framework. In an alternative embodiment, the staples' framework is U-shaped or sinusoidal. The frame of the staples allows for radial deformation resulting in a spring-like effect when a compressed staple is allowed to expand within a vessel and to sustain itself in that expanded condition.

Preferably, the graft is made of a material suitable for permanent placement in the body such as nylon or dacron. Prior to emplacement, the graft is formed to be substantially cylindrical in shape and formed to have a plurality of substantially evenly placed circumferential bifolds along the length thereof. An optional radio-opaque seam on the exterior of the graft may run along the longitudinal axis of the graft in order for the user to observe graft placement through fluoroscopy or by x-ray.

The system for intraluminally engrafting the hollow graft has placement means for emplacing the graft into the lumen and positioning it at a preselected position. The placement means includes a capsule shaped and sized for positioning within the lumen. A hollow tube extends from the capsule to exterior the vessel for manipulation by the user. The graft is retained within the capsule for positioning the graft in the lumen. The placement means includes operation means for removing the graft from the capsule and for subsequently urging the staples into the wall of the lumen.

Preferably, the operation means includes a catheter slidably positioned within the hollow tube to extend from the capsule to exterior the lumen. The catheter desirably has an inflatable membrane operable by means for inflating and deflating the membrane. Pusher means is attached to the catheter and sized for passing through the capsule and for urging the hollow graft with attached staples out of the capsule through an upstream or front end aperture.

After the proximal portion of the graft is removed from the capsule, the inflatable membrane is desirably moved to within the circumference of the proximal staple and inflated to urge wall engaging members of the proximal staple into the wall.

The balloon is then deflated, and the replacement means manipulated to remove the remainder of the graft from the capsule, thus exposing the distal staple. Preferably, the distal staple is placed and affixed in a manner similar to the proximal staple.

The placement means is then removed from the lumen.

BRIEF DESCRIPTION OF THE DRAWINGS

In the drawings, which illustrate the best mode presently contemplated for carrying out the invention, FIG. 1 is a partially cut-away perspective view of an intraluminal graft system of the instant invention;

FIG. 2 is a perspective view of a slightly bent graft device of the instant invention;

DESCRIPTION OF THE ILLUSTRATED EMBODIMENT

Figure 3:
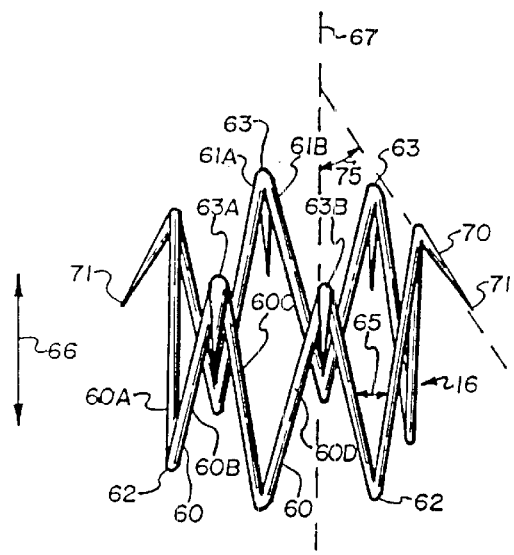
FIG. 3 is an enlarged view of a proximal staple of the instant invention.
Figure 4:
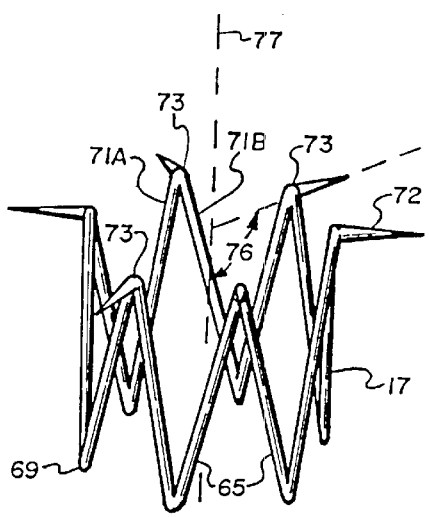
FIG. 4 is an enlarged view of a distal staple of the instant invention.

FIG. 1 illustrates a system 11 for intraluminally placing a prosthesis in a fluid conducting corporeal lumen. The system 11 includes a hollow graft 12 of preselected cross-section and length. The graft 12, as more fully shown in FIG. 2, has a proximal end 14 for placement upstream within a lumen such as a blood vessel. A proximal staple or anchoring element 16 is positioned proximate the proximal end 14 of the graft 12 and is here shown with portions extending through the graft 12 for stapling the graft 12 through the interior wall 13 of the graft 12 into the wall of the lumen. A distal staple or anchoring element 17 is positioned proximate the distal end 88 of the graft 12 and is here shown with portions extending through the graft 12 for stapling the graft 12 to the interior wall 13 of the graft 12 into the wall of the lumen.

The system 11 (FIG. 1) includes placement means for inserting the graft 12 into the lumen and for positioning the graft 12 at a preselected position within the lumen. The placement means includes a capsule 18 which has a front 20 and a back 22. A tube 26 is affixed to the back 22 of the capsule 18 and sized in length 25 to extend exterior the body for manipulation by the user. That is, the tube 26 can be manipulated to move the capsule 18. The placement means also includes operation means, as more fully discussed hereinafter and a wire guide 24.

Figure 6:
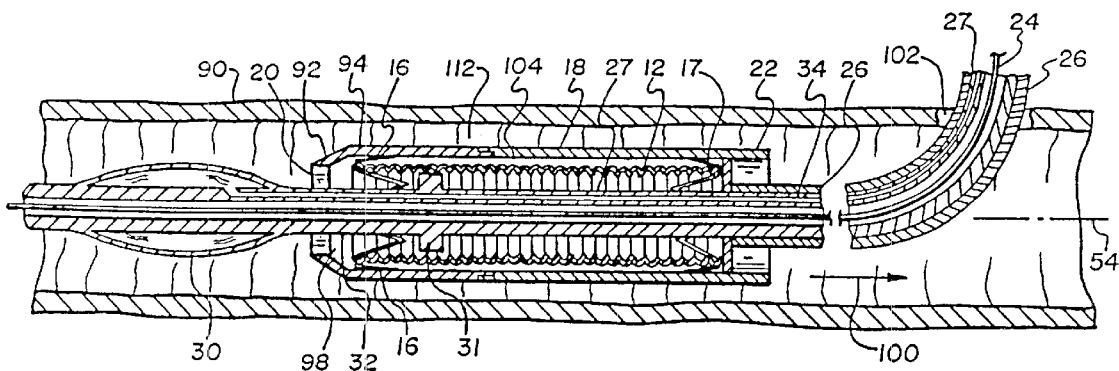
FIGS. 6, 6A and 7 are cross-sectional views of the intraluminal graft device and placement means of the instant invention showing an intraluminal graft being emplaced into a lumen.
Figure 8:
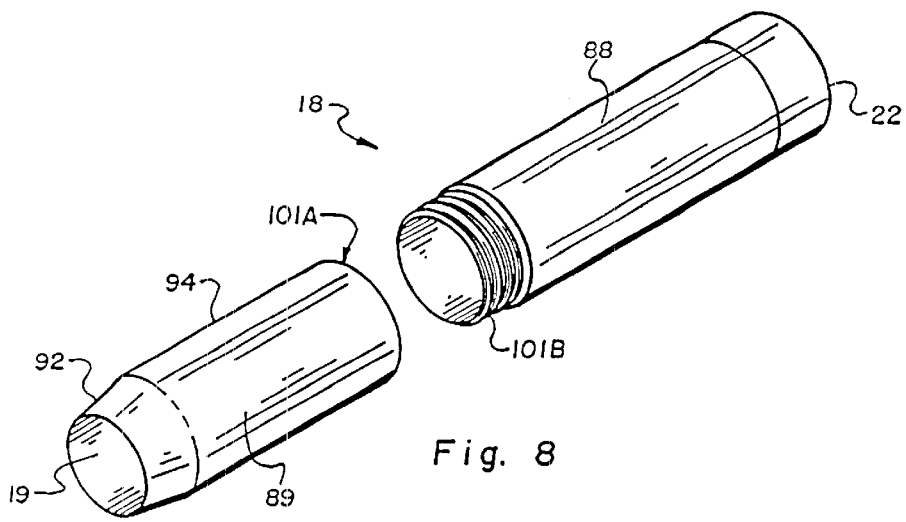
FIG. 8 is a perspective exploded view of an alternate embodiment of the capsule.

The capsule 18 is sized for positioning in the lumen. As can be seen in FIGS. 1, 6 and 8, the capsule is hollow and is also sized in length 21 and cross section 23 to contain the graft 12 for transport through the lumen.

The operation means preferably includes a hollow catheter 27 slidably positionable over the wire guide 24. The catheter 27 has an inflatable membrane ("balloon") 30 positioned proximate the front end 29 of the catheter 27. Means to operate the membrane 30 between inflated and deflated conditions include a channel 34 formed in the wall of catheter 27 to be in fluid communication between the interior of the inflatable membrane 30 and a syringe 38. The channel 34 extends along the length 28 of the catheter 27 to the syringe 38 or other means to insert and remove fluid to inflate and deflate the membrane 30.

A pusher means here shown as a cylindrically shaped button 31 is affixed to and surrounds the catheter 27. It is placed on the catheter 27 behind or downstream of the membrane 30 as best seen in FIGS. 1 And 6. The button 31 is sized to engage the graft 12 with staples within the capsule 18 for urging the graft 12 with staples out of the capsule 18 as more fully discussed hereinafter.

As seen in FIG. 1, syringe mechanism 38 is connected through a connector 40 via an extension tube 42 to the channel 34. Those skilled in the art will recognize that the catheter 27 with the channel 34 and inflatable membrane 30 are very similar in both structure and function to a balloon dilation catheter. It should also be recognized that the syringe is preferably a conventional syringe having a sleeve 44 within which a hand actuated piston 46 is sealably and slidably movable in an inwardly and outwardly direction 48 to insert a fluid via the tube 42 and channel 34 to the membrane 30 to respectively inflate and deflate the membrane 30. The fluid inserted to inflate may be an air or saline solution or such other fluid as desired by the user. Of course the fluid may be extracted to deflate the membrane 30 by operating the piston 46 in an outward direction 48.

The artificial graft 12, shown in FIG. 2, is preferably made of a deformable material having a high tissue ingrowth rate. Various dacron, nylon and teflon materials as well as various polymer materials are regarded as suitable. At present the desired material has been found to be Plasma TFE made by Atrium Medical Corp. of Clinton Drive, Hollis, N.H. (03049).

The graft 12 is preferably formed to have a plurality of substantially evenly spaced circumferential bifolds 50 (similar to the bifolds of a bifold door) along its length 52. The bifolds 50 facilitate both axial 54 and radial 56 deformation of the graft 12. Therefore, when emplaced, the graft 12 may readily conform to the interior shape of the lumen. The length 52 of the graft 12 is selected by the user. Typically, the length 52 of the graft 12 will be selected to be longer than the portion of the lumen to be repaired. The radial 56 or cross-sectional size of the graft 12 is also selected by the user typically to conform substantially to, or be slightly larger than, the interior cross-section of the involved lumen. Since the graft 12 is made of a deformable material with bifolds, it can readily be collapsed or squeezed into the capsule 18.

As shown in FIG. 2, two staples or "securing rings" 16 and 17 are positioned about the circumference of the substantially cylindrically shaped graft 12. Preferred staples are shown in FIGS. 3, 4, 9 and 10.

The staples 16 and 17 are collapsible from an initial diameter to a second smaller diameter. The initial diameter of the staples will be generally the same as the diameters 56 of the graft 12 and the same as or slightly larger than that of the lumen into which the graft 12 with staples 16 and 17 is to be placed. The second diameter will be the same or slightly smaller than inside diameter of the capsule 18. Also, the staples 16 and 17 will generally be made of a metal suitable for use in the body or biocompatible plastic. A stainless steel wire material is presently preferred because of its excellent spring characteristics. As best seen in FIG. 2, the staples 16 and 17 are positioned within the graft 12 and may even be stitched thereto. The staples 16 and 17 are sized to urge the graft 12 outwardly against the inside surface of the lumen into which the graft 12 is placed.

In one embodiment, the proximal staple 16 (FIG. 3) has a plurality of V-shaped support members 60. Each V-shaped support member 60 has an apex 62 with two "free ends" or legs, for example 60A, 60B, 60C and 60D. A free end 61A abuts and is adjoined to the free end 61B of another V-shaped support member 60 at an abutment point 63. The plurality of at least three V-shaped support members 60 are each connected one to another in a generally circular arrangement around the longitudinal axis 67 as shown. With the use of an elastically deformable or spring material, it can be seen that the staple of FIG. 3 can be compressed to make the angle 64 smaller to in turn reduce the staple diameter to fit within the capsule 18.

A wall engaging member 70 is attached to each support member 60 generally along the length 66 of one of the legs 60A, 60B and preferably at or proximate each of at least three abutment points 63 of the proximal staple 16. The preferred wall engaging members 70 are barbs or elongated tine-like members with sharp points 71. The wall engaging members 70 are attached to the support members at an angle 75 which may vary from about 15° to about 135 degrees from the longitudinal or central axis 67 of the proximal staple 16. Preferably the wall engaging members 70 angulate away from the axis 67 in a downstream direction 100 (FIG. 6); and thus the angle 75 is preferably less than 90° and desirably in the range from about 30° to about 60°.

It should be noted that the number or quantity of support members 60 is determined by the axial length 66 of the staple as well as by the cross sectional size of the lumen and in turn the capsule 18. FIG. 3 depicts a plurality of six support members 60 which has been found to be suitable for use in the lumen of selected animals where the lumen is comparable in size to an adult aorta. That is, the lumen has an average or effective diameter of about 12 to 18 millimeters.

It should also be noted that wall engaging members 70 are used to penetrate and hook into the interior surface of the lumen to hold the graft 12 in place. Although in some cases two wall engaging members 70 may be sufficient, it is preferred that at least three be provided. If the lumen is an artery or vein, some deformation is typically experienced so that actual penetration or hooking may be difficult with only two and hooking or penetration is facilitated by the use of three or more. Of course it is most preferred that a wall engaging member be adapted to each support member to facilitate engagement with the wall and also to assist in holding the upstream or proximal end of the graft 12 more securely against the wall of the lumen to minimize fluid (e.g., blood) leakage during the post-therapy healing process.

The proximal staple 16 may be unitarily formed, or may be constructed by interconnecting separate, V-shaped support members having vessel wall engaging members 70. That is, a stainless steel spring wire may be bent to form the apexes 62 and abutment points 63 and soldered or welded at a selected point to be unending as shown. Alternately, separate legs of support members 70 may be welded, glued or soldered together as appropriate to obtain desired strength.

A preferred proximal staple 104 (FIG. 9) is also comprised of a plurality of V-shaped support members 106. Each support member 106 has an apex 108 and two free ends or legs 110. A leg 110A abuts to and is adjoined to the leg 110B of another V-shaped support member 106A at an abutment point 112. The V-shaped support members 106 are connected one to another in a generally circular arrangement around the longitudinal axis 114 to form an unending fence-like arrangement similar to the arrangement of proximal staple 16 (FIG. 3).

Figure 9:
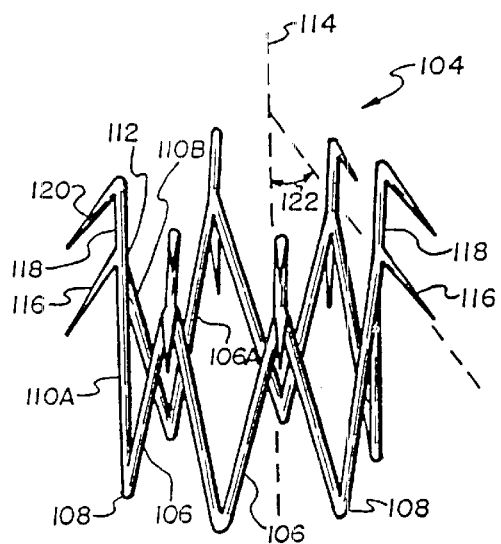
FIG. 9 is an enlarged view of an alternate embodiment of a proximal staple of the instant invention.

In FIG. 9, wall engaging members 116 are adapted to the support members 106 at or near at least three abutment points 112 of the proximal staple 104. However, in the preferred proximal staple 104, an extension member 118 is also mounted to the staple 104 at abutment point 112. Each of these extension members 118 may have an optional and additional wall engaging member 120 attached thereto. The wall engaging members 116, 120 are all mounted to proximal staple 104 at an angle 122 comparable to angle 75 for staple 16 of FIG. 3. The preferred mounting angle of the vessel wall engaging members 116, 120 is from about 30° to about 60 degrees. For ease in insertion into wall of the lumen, wall engaging members 116, 120 are all preferably mounted generally at the same angle 122. That is, the members 116 and 120 are in reality quite small and difficult to mount with precision. Thus the angles may vary as much as 10 degrees. Further, the extension 118 is used to provide additional axial length to the staple 104 without affecting the size of the support members 106 and in turn the second or smaller diameter when collapsed inside capsule 18.

A distal staple 17 (FIG. 4) also preferably comprises a plurality of V-shaped support members 65. Each V-shaped support member is formed to have an apex 69, and two free ends or legs 71A and 71B. A free end 71A abuts and is adjoined to the free end 71B of another V-shaped support member 65 at an abutment point 73. The V-shaped support members 65 of the distal staple 17 are connected one to another in a generally circular arrangement similar to the staple shown in FIG. 3. At a plurality of the abutment points 73 wall engaging members 72 are attached generally at an angle 76 preferably perpendicular to the longitudinal axis 77 of the distal staple. The angle 76 between the wall engaging member 72 and the longitudinal axis 77 may vary between about 45 degrees and about 115 degrees. Preferably, the wall engaging members 72 of the distal staple are sufficiently short so as not to perforate the vessel wall.

Figure 10:
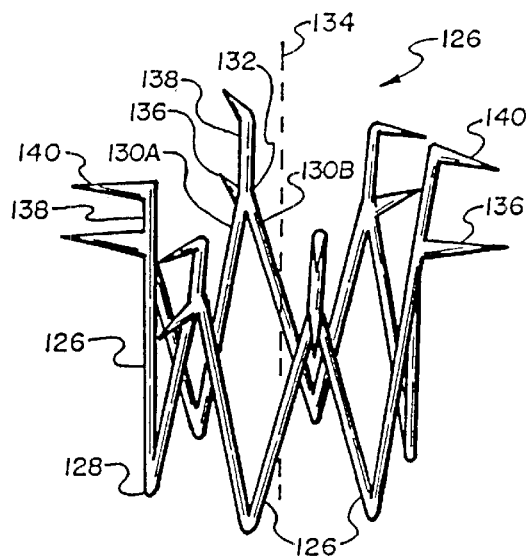
FIG. 10 is an enlarged view of an alternate embodiment of a distal staple of the instant invention.

A preferred distal staple 124 is depicted in FIG. 10. It has a plurality of V-shaped support members 126 formed with an apex 128 and two free legs 130A and 130B. A leg 130A abuts and is adjoined to the leg 130B of an adjacent V-shaped support member 126 at an abutment point 132. The V-shaped support members 126 of distal staple 124 connect one to another in a generally circular arrangement about axis 134 to form a fence-like arrangement similar to the staples shown in FIGS. 3 and 4.

Wall engaging members 136 are mounted at or near at least three abutment points 132 of distal staple 124. Distal staple 124 has extension members 138 mounted at a plurality of abutment points 132 with a separate wall engaging member 140 mounted thereto, all similar to that shown for staple 104 (FIG. 9). As in distal staple 17, the wall engaging members 136, 140 are mounted to the staple 124 at an angle which may vary from about 45° to about 115°. Preferably the angle varies from about 75 degrees to about 105 degrees, and is most desirably generally perpendicular to axis 134. As in proximal staple 104, both the corresponding wall engaging members 136, 140 are mounted at the same angles to the staple 124.

Figure 11:
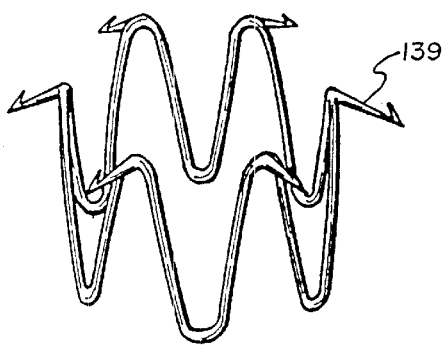
FIG. 11 is an enlarged partial view of an alternate embodiment of a staple of the instant invention.

The support members may also be U-shaped, as shown in FIG. 11 for all of the aforementioned staples 16, 17, 104 and 126. The arrangement would thus appear generally sinusoidal. In another alternative embodiment, the vessel wall engaging members 70, 72, 116, 120, 136 and 140 of FIGS. 3, 4, 9 and 10 may be barbed like fish hooks similar to barbed member 139 shown in FIG. 11.

Figure 7:
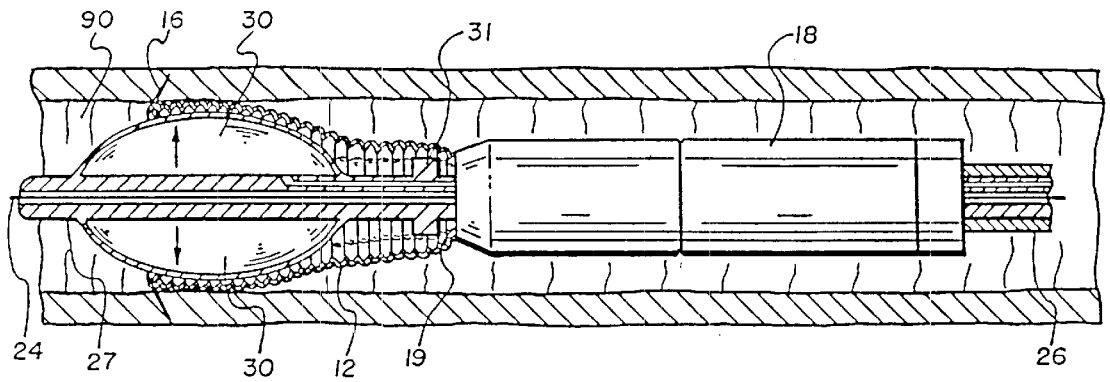

Referring now to FIG. 6, portions of the system 11 (FIG. 1) for intraluminal engrafting are shown cross-sectionally within a lumen 90. The system 11 including the graft 12 and capsule 18 may be constructed in a variety of different sizes in order to accommodate and be compatible with a variety of differently sized (in cross-section) corporeal lumens. In FIGS. 6 and 7, the capsule 18 is shown to be smaller than the lumen 90 so that the various surfaces may be better illustrated. Typically, the cross-sectional size (i.e., area normal to axis 54) of the pertinent system components such as the capsule 18 and graft 12 are selected to be substantially the same as or slightly smaller than the lumen 90. It should be further recognized that the corporeal lumen 90 illustrated is substantially circular in cross-section. However, lumens such as blood vessels may vary widely in cross-section along their length but will elastically deform to receive the capsule 18 and other components of the system 11. The lumens are also not straight in that they have many curves as they course throughout the body.

Figure 5:
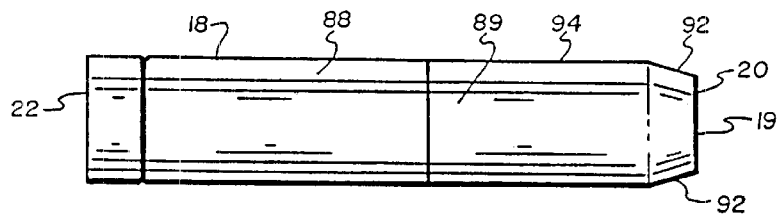
FIG. 5 is an enlarged side view of a capsule of the instant invention.

As shown in FIG. 5, the capsule 18 preferably has a rounded or tapered edge surface 92 between the side surface 94 and the front 20. The tapered surface 92 facilitates entry into and positioning within the lumen 90 by providing a contact surface to stretch the lumen especially in those places where the lumen 90 may be constricted or smaller in cross-section than the capsule 18 and the graft 12. A corporeal lumen such as a blood vessel or artery can stretch and deform. The tapered surface 92 can urge or force the deformation desired in order to facilitate placement as the capsule 18 is urged into and through the lumen 90 by exerting an emplacing force on the exterior end 96 of the tube 26.

The inside of the capsule 18 has a smooth bore cavity 98 (FIG. 6) formed therein sized to receive the graft 12. As can be seen, the catheter 27 may be centrally positioned within the cavity 98. Lead or guide wire 24 may be positioned within the lumen 90 in a manner known in the art and then threaded through the interior of the catheter 27. The tube 26 is affixed to the capsule 18 at its back 22 to extend rearwardly or downstream 100 through an opening 102 made in the lumen for inserting the pertinent components of the system 11. The catheter 27 can slidably mate within the hollow tube 26.

The capsule 18 as shown in FIG. 5 has an aperture 19 formed in its front end 20 which is sized for passage of the graft 12 with staples 16 and 17. That is, the graft 12 with staples 16 and 17 are urged through aperture 19 for placement in the lumen 90 as hereinafter discussed. The capsule 18 is formed of any medically acceptable material. A variety of nylon and teflon materials are known to be acceptable along with selected metals. It is here preferred to use stainless steel as the staples are easier to urge outwardly through the aperture 19. The connection means is structured to provide a smooth exterior surface as seen in FIG. 5.

As shown in FIG. 6, the graft 12 is positioned within the cavity 98 of the capsule 18. The graft 12 and staples 16 and 17 are preferably sized as hereinbefore discussed when in an undeformed condition to be slightly larger in cross-section than the cross-section of the lumen 90 and yet deformable to fit into the cavity 98. An external or radial force is thereby exerted outwardly against the interior surface 160 of the cavity 98 to retain the graft 12 within the capsule 18. Further, the lumen engaging portion of the disclosed staples may frictionally engage the interior surface 104 of the capsule 18 to further restrain and retain the graft 12 within the cavity during placement in the lumen.

As shown in FIG. 8, the capsule 18 preferably consists of two connecting tubular portions 152, 89 which mate together by connection means which are here shown to be a coacting male threaded member 101B and female threaded member 101A. Such a construction is used to aid in placing the graft 12 within the capsule 18 so as to house it within the capsule 18. The proximal portion 89 of the capsule 18 can be disconnected from the distal portion 152. The distal end 15 of graft 12 is then positioned within the distal portion 152 of the capsule 18. The proximal end 14 of the graft 12 is similarly positioned into the proximal portion 89 of the capsule which is then connected to the distal portion 152. The catheter 27 is then extended into the capsule and the graft 12. The connection means is preferably selected to minimize the amount of relative rotation between the proximal and distal portions 152, 89 to minimize twisting of the graft 12.

Whatever the form of the capsule 18, it can be seen in FIG. 6 that an opening 102 is formed in the lumen 90 such as an artery, vessel or other similar corporeal lumen. A guide wire 24 may be then sequentially inserted therethrough and manipulated to a desired location. An appropriately sized capsule 18 with graft 12 are inserted through the opening 102 and into the lumen 90 over the guide wire 24. With the graft 12 in position as shown in FIG. 6, the capsule 18 is urged in an upstream direction by exerting a positioning force on the exterior 108 of tube 26 (FIG. 1). Then the catheter 27 may be inserted. Of course, the guide wires 24, catheter 27, and tube 26 are each sized to be of sufficient length 25 and 28 so that the capsule 18 and graft 12 may be positioned through the lumen 90 to a desired position which may be some distance from the entry point 102. It will also be recognized by those skilled in the art that appropriate radiological techniques such as fluoroscopy can be used to assist the user in positioning the capsule 18 and in turn the graft 12 at a precise desired position within the lumen 90. This position, in all likelihood, would be a diseased or damaged portion of the lumen 90 which is in need of repair. Upon reaching the desired position within the lumen 90, further forward or upstream movement within the lumen 90 is stopped. A clamp or other means may be placed about the catheter 27 outside the vessel to prevent movement of the catheter 27 relative to the tube 26. The tube 26 may also be secured or held by the user as desired.

Figure 6A:
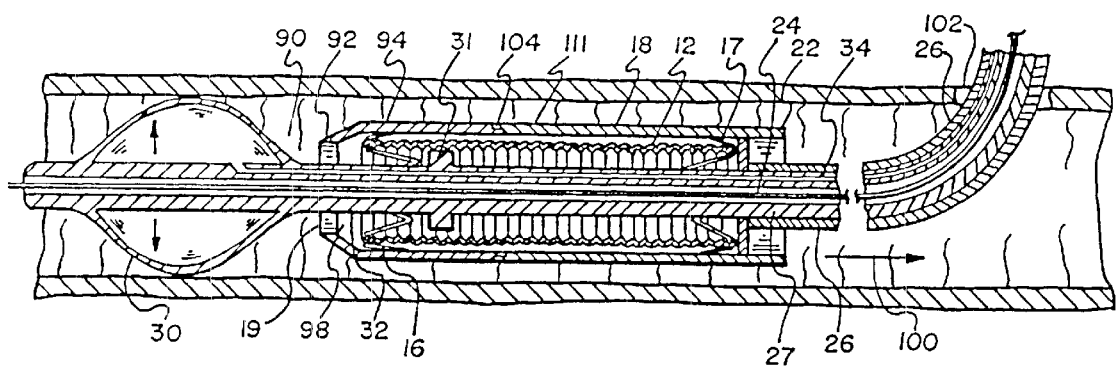

The pusher button 31 and catheter 27 are then used to urge the graft forwardly or upstream through the aperture 19. The proximal end 14 of the graft 12 first leaves the capsule 18 as the pusher button engages portions of the distal end of the compressed proximal staple 16. For purposes of this illustration staples 16 and 17 (FIGS. 3 and 4) will be used. However, staples 104 and 124 could be substituted in their place as could any other equivalent staple. The pusher button 31 has a diameter small enough to fit through the tube 26 and into the graft 12 and through aperture 19 of the capsule 18. The catheter 27 is maintained in a steady position while the tube 26 is moved downstream from the proximal staple 16. The balloon 30 may be inflated as shown in FIG. 6A to provide a holding force and resist relative movement as to the lumen 90. The pusher button 31 makes contact with pieces of the compressed proximal staple 16 urging the proximal staple through the aperture 19 of the capsule 18.

As the proximal staple 16 is pushed through the aperture 19 of the capsule 18 it springs open or expands, causing the wall engaging members 70 to contact with the wall of the lumen 90. After the proximal staple 16 has been completely removed from the capsule 18 and the wall engaging members 70 have made initial contact with the wall, the inflatable membrane 30 is moved to within the circumference of proximal staple 16 and graft 12. The inflatable membrane ("balloon") 30 is then inflated (see FIG. 7) by use of the inflation means 36 to urge the wall engaging members 70 into the wall surface of the lumen 90 to firmly lodge the proximal staple 16 and the graft 12 in place.

The capsule 18 is then moved downstream 100 even more to free the distal portion 15 of the graft 12 from the capsule 18 and exposing the distal staple 17 and wall engaging members 72 to the interior surface of the lumen 90. The balloon 30 may be deflated, moved to register with the staple 16 and inflated to ensure that the graft 12 remains securely positioned. After the distal portion 15 is free, the balloon 30 is deflated and moved to register with the distal staple 17. The balloon 30 is then reinflated to urge the wall engaging members 72 of the distal staple 17 into the wall thereby firmly securing the distal staple 17 and distal end 15 of the graft to the lumen 90. An angiogram may then be performed if desired through the balloon catheter to determine the patency and security of the graft 12. Other balloon catheters may be used which do not have the main lumen to perform the angiogram. Thus, the guide wire is not then used and a separate angiogram catheter needed to perform a subsequent angiogram.

Figure 8A:
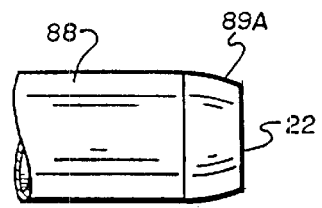
FIG. 8A is a partial perspective view of an alternate capsule.

The balloon 30 is then deflated and the tube 26 with capsule 18 is withdrawn from within the lumen 90. After removing the tube 26 in its entirety, the catheter 27 is thereafter removed and the opening 102 sealed. The back 22 of the capsule 18 may be formed to have a slightly rounded edge 89A to facilitate removal as shown in FIG. 8A.

After emplacement, it can be seen that the pressure of the lumen fluid, for example, blood, forces the graft 12 against the lumen interior surface 154, helping to hold the graft 12 in place. The bifolds 50 of the graft 12 permit deformation of the graft 12 to conform to the interior surface 154 of the lumen and provide for flexibility to bend and stretch with the natural lumen. Further, the bifolds 50 act somewhat as a mechanical labyrinth seal to reduce leakage between the interior surface 154 of the lumen and the exterior surface 84 of the graft 12. That is, the internal pressure of the fluid within the lumen 90 holds the graft 12 in place and assists the staples 16 and 17 in preventing leakage at both ends of the graft 12.

In operation, it should be noted that the system 11 with the graft 12 is inserted into the lumen 90 using accepted surgical techniques. For example, an opening could be made through the leg to reach the main artery of a human being. Thereafter, the system 11 could be used as above described to emplace an artificial graft within the main artery as far interior the body as the myocardial or great artery area. This technique therefore avoids major surgery in which the chest or abdomen is penetrated for repair of the aorta, vena cava or the like.

The components of system 11 are, of course, made of anatomically compatible substances. For example, the tube 26 and inflatable membrane 30 are made of a substantially chemically compatible plastic. The catheter 27 is made of a material such as Teflon to be flexible and sized in appropriate diameter and length to facilitate placement of the graft 12 in the desired location within the lumen 90.

Use of the system 11 with the graft 12 herein described may preclude the need for major surgery to repair a vessel, such as a blood vessel or artery in the great artery area. It can also be used to repair other vessels or ductiles within the body of a human being or animal. Use of the system may thus reduce the morbidity rates associated with major surgery. It also facilitates rapid repair of defective or damaged vessels at relatively low cost and risk. The system is mechanically simple and reliable and also useful for treating trauma victims in an emergency context.

It may be noted that the system 17 herein described, including the graft 12, are merely illustrative of the application of the principles of the invention. Reference herein to details of the illustrated embodiments is not intended to limit the scope of those claims which themselves recite those features regarded as essential to the invention.

I claim:

1. A system for placement within vasculature, comprising:
   a graft having a front end;
   an elongate catheter; and
   a balloon catheter, said balloon catheter having an inflatable portion;
   wherein said inflatable portion is positioned entirely beyond said front end of said graft when said system is configured for insertion into vasculature.

2. The system of claim 1, said elongate catheter further comprising a capsule, said capsule being dimensioned to receive said graft.

3. The system of claim 1, said elongate catheter further comprising a tube which slidably receives a portion of said balloon catheter.

4. The system of claim 1, wherein said graft is a graft assembly.

5. The system of claim 4, said graft assembly further comprising a tubular body and at least one attachment system.

6. The system of claim 5, wherein said attachment system embodies a plurality of V-shaped support members connected together in a circular arrangement.

7. The system of claim 6, said attachment system further comprising at least one wall engaging member attached to one of said V-shaped members.

8. The system of claim 1, the elongate catheter including structure that encapsulates the graft.

9. The system of claim 1, the elongate catheter further includes an exit port, said exit port being positioned at a front end of the catheter.

* * * * *

UNITED STATES PATENT AND TRADEMARK OFFICE
CERTIFICATE OF CORRECTION

PATENT NO.   : 6,544,268 B1
DATED        : April 8, 2003
INVENTOR(S)  : Harrison M. Lazarus It is certified that error appears in the above-identified patent and that said Letters Patent is hereby corrected as shown below:

Column 8,
Line 15, change "160", to read -- 150 --.

Column 10,
Line 27, change "17", to read -- 11 --.
Line 36, after "catheter" and before ";", add -- said elongated catheter further comprises a pusher device, said pusher device configured to engage said graft --.

Signed and Sealed this

Fifth Day of August, 2003

JAMES E. ROGAN
*Director of the United States Patent and Trademark Office*